(12) United States Patent
Fukami et al.

(10) Patent No.: US 6,867,214 B1
(45) Date of Patent: Mar. 15, 2005

(54) QUINAZOLINE DERIVATIVES AND PHARMACEUTICAL APPLICATIONS THEREOF

(75) Inventors: Harukazu Fukami, Kyoto (JP); Akiko Ito, Rockville, MD (US); Seiichi Imajo, Ikeda (JP)

(73) Assignee: Daiichi Suntory Pharma Co., Ltd., Tokyo (JP)

( * ) Notice: Subject to any disclaimer, the term of this patent is extended or adjusted under 35 U.S.C. 154(b) by 0 days.

(21) Appl. No.: 09/763,213
(22) PCT Filed: Aug. 20, 1999
(86) PCT No.: PCT/JP99/04503
§ 371 (c)(1), (2), (4) Date: Apr. 12, 2001
(87) PCT Pub. No.: WO00/10982
PCT Pub. Date: Mar. 2, 2000

(30) Foreign Application Priority Data

Aug. 21, 1998 (JP) .............................. 10/235633

(51) Int. Cl.$^7$ .................... C07D 239/96; A61K 31/517; A61P 11/06; A61P 19/02
(52) U.S. Cl. .................... 514/266.3; 544/285; 544/105; 564/42
(58) Field of Search ................. 544/285, 105; 514/266.3

(56) References Cited

U.S. PATENT DOCUMENTS

| 5,304,560 A | 4/1994 | Shimazaki et al. ......... 514/259 |
| 5,814,631 A * | 9/1998 | Fukami et al. ............ 514/234.5 |

FOREIGN PATENT DOCUMENTS

| EP | 0 795 548 | 9/1997 |
| HU | 3243/91 A | 5/1992 |
| JP | 05 169832 | 7/1993 |
| WO | 97/45400 | 12/1997 |

OTHER PUBLICATIONS

Y. Liao, et al., "The chymase–angiotensin system in humans: Biochemistry, molecular biology and potential role in cardiovascular diseases", Canadian Journal of Cardiology, vol. 11, No. Suppl. F., pp. 13F–19F.

S. Niwata et al., "Substituted 3-(Phenylsulfonyl)-1-phenylimidazolidine-2,4-dione Derivatives as Novel Nonpeptide Inhibitors of Human Heart Chymase", Journal of Medicinal Chemistry, vol. 40, No. 14, 1997, pp. 2156–2163.

* cited by examiner

Primary Examiner—Mark L Berch
Assistant Examiner—Kahsay Habte
(74) Attorney, Agent, or Firm—Burns, Doane, Swecker & Mathis, L.L.P.

(57) ABSTRACT

A quinazoline derivative having formula (1) and a pharmaceutically acceptable salt thereof:

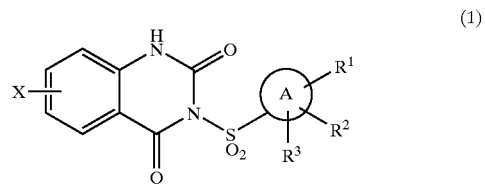

wherein the ring A represents an aryl group, which derivative has a chymase inhibitory activity and suppresses the exacerbation of vascular permeability induced by chymase, and a pharmaceutical composition containing the same as an essential ingredient. These compounds are useful for treatment of allergic diseases, rheumatic diseases, and cardiac and circulatory system diseases which are due to the abnormal exacerbation of Angiotensin II production.

17 Claims, No Drawings

QUINAZOLINE DERIVATIVES AND PHARMACEUTICAL APPLICATIONS THEREOF

TECHNICAL FIELD

The present invention relates to a quinazoline derivative having a chymase inhibitory activity and a pharmaceutically acceptable salt thereof and to a pharmaceutical composition and a chymase inhibitor having the same as an effective ingredient. The present invention also relates to a method for producing the quinazoline derivative and a synthesis intermediate thereof.

BACKGROUND ART

Chymase is known to be present in secretory granules of mast cells (MC), which are closely related to inflammation, as one type of inflammatory cell. Further, human chymase similarly is mainly present broadly in MCs in the skin, heart, vascular walls, intestines, and other tissue (*Mast Cell Proteases in Immunology and Biology*; Caughey, G. H., ed; Marcel Dekker, Inc.: New York, 1995). Human MCs are known to increase with bronchial asthma, allergic dermatitis and other allergic diseases, arteriosclerosis (Kaartinen et al., *Circulation*, 1994, 90, 1669), myocardial infarction (Kovanen et al., *Circulation*, 1995, 92, 1084), and other circulatory system diseases and rheumatoid arthritis (Gotis-Graham et al., *Arthritis Rheum.*, 1997, 40, 479). Further, it has been reported that the genetic polymorphism of chymase is correlated to the onset of eczema (Mao et al., Lancet, 1996, 348, 581). Human chymase produces angiotensin II (Ang II) specifically from angiotensin I (Ang I) in the same way as an angiotensin converting enzyme. Ang II is closely related to regulation of the blood pressure, diuretic regulation, the migration and proliferation of smooth muscle cells etc. in the cardiovascular system tissue, the growth of the extracellular matrix, and other hypertrophy and remodeling of the cardiovascular system (Hideki Okunishi; *Naibunpitsu-Tonyobyoka*, 1996, 3(6), 535). Human chymase is reported to have the following actions due to its protease activity in addition to production of Ang II: 1) degradation of the extracellular matrix (Vartio et al., *J. Biol. Chem.*, 1981, 256, 471), activation of collagenase (Kovanen et al., *J. Biol. Chem.*, 1994, 269, 18134), and production of collagen (Kofford et al., *J. Biol. Chem.*, 1997, 272, 7127); 2) causing release of inflammatory cytokine, for example, release of TGF β1 from extracellular matrix (Taipale et al., *J. Biol. Chem.*, 1995, 270, 4689) and production of IL-1β (Mizutani. et al., *J. Exp. Med.*, 1991, 174, 821); and 3) activation of stem cell factor (SCF) causing differentiation and proliferation of MCs (Longley et al., *Pro. Nat. Acad. Sci.*, 1997, 94, 9017). Further, rat MC chymase is known to cause degranulation of MCs through IgE receptors, release chemical mediators such as histamine, partially hydrolyze the apolipoproteins of low density lipoproteins (LDL) to make modified LDL incorporated into macrophages, and convert the macrophages to foam cells (*Mast Cell Proteases in Immunology and Biology*; Caughey, G. H., Ed; Marcel Dekker, Inc.: New York, 1995).

On the other hand, low molecular chymase inhibitors have already been shown in print (*Protease Inhibitors*; Barrett. et. al., eds.; Elssevier Science B. V.: Amsterdam, 1986). Further, recently, as peptide inhibitors for human chymase, there have been α-keto acid derivatives (WO-A-93-25574, *Proc. Natl. Acad. Sci. USA*, 1995, 92, 6738) and α,α-difluoro-β-keto acid derivatives (JP-A-9-124691), while as peptide-mimetic inhibitors, there are trifluoromethylketone derivatives (WO-A-96-33974, JP-A-10-53579), and α,α-difluoro-β-keto acid derivatives (JP-A-10-7661), while as nonpeptide inhibitors, there have been imidazolinedione derivatives (*J. Med. Chem.*, 1997, 40, 2156), quinazoline derivatives (WO 97-11941), phenyl ester derivatives (JP-A-10-87567), etc. There are no examples however of commercialization as medicaments.

The above reports relating to chymase suggest that chymase plays an important role in the process of inflammation, repair, and cure of damaged tissue. That is, it breaks down the extracellular matrix at the inflammatory tissue, releases and activates inflammatory cytokine, causes cell migration and proliferation, reproduces the extracellular matrix, and makes the tissue repair. The excess reactions in this process are believed to be linked to various diseases. Therefore, by inhibiting chymase and suppressing the exacerbation of vascular permeability induced by chymase, utilization as a medicament for prevention and a medicament for treatment of allergic diseases such as bronchial asthma, cnidosis, atopic dermatitis, mastocytosis, scleriasis, rheumatic diseases such as arthritis, cardiac and circulatory system diseases arising due to abnormal exacerbation of Ang II production, for example, cardiac insufficiency, hypercardia, stasis cardiac diseases, hypertension, arteriosclerosis, peripheral circulatory disorders, revasoconstriction after PCTA, diabetic renal disorders or non-diabetic renal disorders, coronary diseases including myocardial infarction, angioendothelia, or vascular disorders accompanying arterialization or atheroma may be given as examples.

DISCLOSURE OF INVENTION

Accordingly, the object of the present invention is to provide a compound having a chymase inhibitory activity and capable of suppressing the advance of vascular permeability induced by chymase and useful as a pharmaceutical composition and a pharmaceutical composition containing the same.

In accordance with the present invention, there is provided a quinazoline derivative having the following formula (1) and a pharmaceutically acceptable salt thereof:

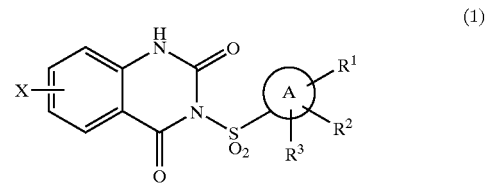

(1)

wherein, the ring A represents an aryl group $R^1$ represents a hydroxyl group, an amino group, a $C_1$ to $C_4$ lower alkylamino group which may be substituted with a carboxylic acid group, a $C_7$ and $C_{10}$ lower aralkylamino group which may be substituted with a carboxylic acid group, an amino group acylated with a $C_1$ to $C_4$ lower aliphatic acid which may be substituted with a carboxylic acid group, an amino group acylated with an aromatic ring carboxylic acid which may be substituted with a carboxylic acid group, an amino group acylated with a heteroaromatic ring carboxylic acid which may be substituted with a carboxylic acid group, an amino group sulfonylated with a $C_1$ to $C_4$ lower alkanesulfonic acid which may be substituted with a carboxylic acid group, an amino group sulfonylated with an aromatic ring sulfonic acid which may be substituted with a carboxylic acid group, an amino group sulfonylated with a heteroaromatic ring sulfonic acid which may be substituted with a carboxylic acid group, a $C_1$ to $C_4$ lower alkyl group substituted with a carboxylic acid group, or a $C_2$ to $C_4$ lower alkenyl group which may be substituted with a carboxylic acid group.

$R^2$ and $R^3$ may be the same or different and represent a hydrogen atom, an unsubstituted or substituted $C_1$ to $C_4$ lower alkyl group, a halogen atom, a hydroxyl group, a $C_1$ to $C_4$ lower alkoxyl group, an amino group, an unsubstituted or substituted $C_1$ to $C_4$ lower alkylamino group, an unsubstituted or substituted $C_7$ to $C_{10}$ aralkylamino group, an amino group acylated with a $C_1$ to $C_4$ lower aliphatic acid which may be substituted with a carboxylic acid group, an amino group acylated with an aromatic ring carboxylic acid which may be substituted with a carboxylic acid group, an amino group acylated with a heteroaromatic ring carboxylic acid which may be substituted with a carboxylic acid group, an amino group sulfonylated with a $C_1$ to $C_4$ lower alkanesulfonic acid which may be substituted with a carboxylic acid group, an amino group sulfonylated with an aromatic ring sulfonic acid which may be substituted with a carboxylic acid group, an amino group sulfonylated with a heteroaromatic ring sulfonic acid which may be substituted with a carboxylic acid group, or a carboxylic acid group or when the ring A is a benzene ring, $R^1$ and $R^2$ may form, together with the substituting benzene ring, a fused heterocyclic ring which may be substituted with a carboxylic acid and in which the carbon atom in the ring may form a carbonyl group and $R^3$ is the same as defined above; and X represents a hydrogen atom, a $C_1$ to $C_4$ lower alkyl group, a $C_1$ to $C_4$ lower alkoxy group, a halogen atom, a hydroxyl group, an amino group, or a nitro group.

The present compound has a human chymase inhibitory activity and suppresses the exacerbation of vascular permeability induced by chymase and is useful as a pharmaceutical composition for the prevention or treatment of allergic diseases or rheumatic diseases caused by the increase in mast cells or cardiac and circulatory system diseases due to the abnormal exacerbation of angiotensin II production.

In accordance with the present invention, there is also provided a pharmaceutical composition comprising, as an effective ingredient, the above-mentioned quinazoline derivative or the pharmaceutically acceptable salt thereof and a pharmaceutically acceptable conventional carrier therefor.

In accordance with the present invention, there is further provided a method for producing the quinazoline derivative and a synthesis intermediate thereof.

BEST MODE FOR CARRYING OUT THE INVENTION

In the general formula (1), preferable examples of the aryl group represented by the ring A are a benzene ring and a naphthalene ring.

Preferable examples of the $C_1$ to $C_4$ lower alkylamino group which may be substituted with the carboxylic acid group and the $C_7$ to $C_{12}$ lower aralkylamino group which may be substituted with a carboxylic acid group represented by $R^1$ are a methylamino group, an ethylamino group, a propylamino group, a butylamino group, a carboxymethylamino group, a carboxyethylamino group, a carboxypropylamino group, a carboxybutylamino group, a benzylamino group, a phenetylamino group, a phenylpropylamino group, a phenylbutylamino group, a carboxybenzylamino group, a carboxyphenetylamino group, a carboxyphenylpropylamino group, a carboxyphenylbutylamino group, etc.

Preferable examples of the amino group acylated with a $C_1$ to $C_4$ lower aliphatic acid which may be substituted with a carboxylic acid group, the amino group acylated with an aromatic ring carboxylic acid which may be substituted with a carboxylic acid group, and the amino group acylated with a heteroaromatic ring carboxylic acid which may be substituted with a carboxylic acid group represented by $R^1$ are a formylamino group, an acetylamino group, a propionylamino group, a butyrylamino group, a benzoylamino group, a naphthoylamino group, a pyridinecarbonylamino group, a pyrrolecarbonylamino group, a carboxyacetylamino group, a carboxypropionylamino group, a carboxybutyrylamino group, a carboxybenzoylamino group, a carboxynaphthoylamino group, a carboxypyridinecarbonylamino group, a carboxypyrrolecarbonylamino group, etc.

Preferable examples of the amino group sulfonylated with a $C_1$ to $C_4$ lower alkanesulfonic acid which may be substituted with a carboxylic acid group, the amino group sulfonylated with an aromatic ring sulfonic acid which may be substituted with a carboxylic acid group, and the amino group sulfonylated with a heteroaromatic ring sulfonic acid which may be substituted with a carboxylic acid group represented by $R^1$ are a methanesulfonylamino group, an ethanesulfonylamino group, a propanesulfonylamino group, a butanesulfonylamino group, a benzenesulfonylamino group, a naphthalenesulfonylamino group, a pyridinesulfonylamino group, a pyrrolesulfonylamino group, a carboxymethanesulfonylamino group, a carboxyethanesulfonylamino group, a carboxypropanesulfonylamino group, a carboxybutanesulfonylamino group, a carboxybenzenesulfonylamino group, a carboxynaphthalenesulfonylamino group, a carboxypyridinesulfonylamino group, a carboxypyrrolesulfonylamino group, etc.

Preferable examples of the $C_1$ to $C_4$ lower alkyl group substituted with a carboxylic acid group represented by $R^1$ are an acetic acid group, a propionic acid group, a butyric acid group, a valeric acid group, etc.

Preferable examples of the $C_2$ to $C_4$ lower alkenyl group substituted with a carboxylic acid group represented by $R^1$ are an acrylic acid group, a crotonic acid group, etc.

Preferable examples of the unsubstituted or substituted $C_1$ to $C_4$ lower alkyl group represented by $R^2$ or $R^3$ are a straight-chain alkyl group such as a methyl group, an ethyl group, a n-propyl group, and a n-butyl group and a branched alkyl group such as an isopropyl group, a sec-butyl group, and a t-butyl group.

Preferable examples of the substituent group of the $C_1$ to $C_4$ lower alkyl group are a carboxylic acid group, a halogen atom such as a fluorine atom and a chlorine atom, a $C_1$ to $C_4$ lower alkoxy group, an amino group, a methylamino group, a dimethylamino group, a carboxymethylamino group, a carboxyethylamino group, etc.

Preferable examples of the halogen atom represented by $R^2$ or $R^3$ are a fluorine atom, a chlorine atom, a bromine atom and an iodine atom.

Preferable examples of the $C_1$ to $C_4$ lower alkoxyl group represented by $R^2$ or $R^3$ are a straight-chain alkyloxy group such as a methoxy group, an ethoxy group, a n-propyloxy group, and a n-butoxy group and a branched alkyloxy group such as an isopropyloxy group, a sec-butoxy group, and a t-butoxy group.

Preferable examples of the unsubstituted or substituted $C_1$ to $C_4$ lower alkylamino group represented by $R^2$ or $R^3$ are a methylamino group, an ethylamino group, a propylamino group, a butylamino group, etc.

Preferable examples of the substituent group of the $C_1$ to $C_4$ lower alkylamino group are a carboxylic acid group, a halogen atom such as a fluorine atom and a chlorine atom, a $C_1$ to $C_4$ lower alkoxyl group, etc.

Preferable examples of the unsubstituted or substituted $C_7$ to $C_{12}$ lower aralkylamino group represented by $R^2$ or $R^3$ are a benzylamino group, a phenetylamino group, a phenylpropylamino group, a phenylbutylamino group, etc.

Preferable examples of the substituent group of the aralkylamino group are a carboxylic acid group, a halogen atom such as a fluorine atom and a chlorine atom, a $C_1$ to $C_4$ lower alkoxyl group, etc.

Preferable examples of the amino group acylated with a $C_1$ to $C_4$ lower aliphatic acid which may be substituted with a carboxylic acid group, the amino group acylated with an aromatic ring carboxylic acid which may be substituted with a carboxylic acid group, and the amino group acylated with a heteroaromatic ring carboxylic acid which may be substituted with a carboxylic acid group represented by $R^2$ or $R^3$ are a formylamino group, an acetylamino group, a propionylamino group, a butyrylamino group, a benzoylamino group, a naphthoylamino group, a pyridinecarbonylamino group, a pyrrolecarbonylamino group, a carboxyacetylamino group, a carboxypropionylamino group, a carboxybutyrylamino group, a carboxybenzoylamino group, a carboxynaphthoylamino group, a carboxypyridinecarbonylamino group, a carboxypyrrolecarbonylamino group, etc.

Preferable examples of the amino group sulfonylated with a $C_1$ to $C_4$ lower alkanesulfonic acid which may be substituted with a carboxylic acid group, the amino group sulfonylated with an aromatic ring sulfonic acid which may be substituted with a carboxylic acid group, and the amino group sulfonylated with a heteroaromatic ring sulfonic acid which may be substituted with a carboxylic acid group represented by $R^2$ or $R^3$ are a methanesulfonylamino group, an ethanesulfonylamino group, a propanesulfonylamino group, a benzenesulfonylamino group, a naphthalenesulfonylamino group, a pyridinesulfonylamino group, a pyrrolesulfonylamino group, a carboxymethanesulfonylamino group, a carboxyethanesulfonylamino group, a carboxypropanesulfonylamino group, a carboxybenzenesulfonylamino group, a carboxynaphthalenesulfonylamino group, a carboxypyridinesulfonylamino group, a carboxypyrrolesulfonylamino group, etc.

Preferable examples of the fused heterocyclic ring which may be substituted with a carboxylic acid and in which the carbon atom in the ring may form a carbonyl group which $R^1$ and $R^2$ form together with the substituting benzene ring when the ring A is a benzene ring, are a tetrahydroquinoline ring and a benzoxazine ring, for example, a tetrahydroquinoline, a benzoxazine, a quinoxaline, a benzodioxane, a carboxytetrahydroquinoline, a carboxybenzoxazine, a carboxyquinoxaline, a carboxybenzodioxane, etc.

Preferable examples of the $C_1$ to $C_4$ lower alkyl group represented by X are a straight-chain alkyl group such as a methyl group, an ethyl group, a n-propyl group, and a n-butyl group and a branched alkyl group such as an isopropyl group, a sec-butyl group, and a t-butyl group.

Preferable examples of the $C_1$ to $C_4$ lower alkoxyl group represented by X are a straight-chain alkyloxy group such as a methoxy group, an ethoxy group, a n-propyloxy group, and a n-butoxy group and a branched alkyloxy group such as an isopropyloxy group, a sec-butoxy group, and a t-butoxy group.

Preferable examples of the halogen atom represented by X, are a fluorine atom, a chlorine atom, a bromine atom and an iodine atom.

Further, examples of a pharmaceutically acceptable salts are an acid salt such as a hydrochloric acid salt, a methanesulfonic acid salt, and a trifluoroacetic acid salt and an alkali metal salt such as a sodium salt and a potassium salt.

The quinazoline derivative having the formula (1) according to the present invention may, for example, be synthesized by the following Synthesis Method (A) or (B).

Synthesis Method (A)

A compound having the formula (2):

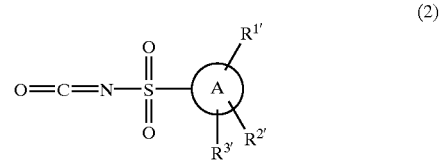

(2)

wherein the ring A is the same as defined above and $R^{1'}$, $R^{2'}$ and $R^{3'}$ represent $R^1$, $R^2$ and $R^3$, which may be protected with a protecting group, respectively, and $R^1$, $R^2$ and $R^3$ represent the same as defined above is reacted with an anthranilic acid derivative having the formula (3):

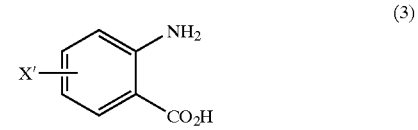

(3)

wherein X' represents X, which may be protected with a protecting group, and X represents the same as defined above using the method described, for example, in JP-A-6-199839 to obtain a sulfonylurea derivative having the formula (4):

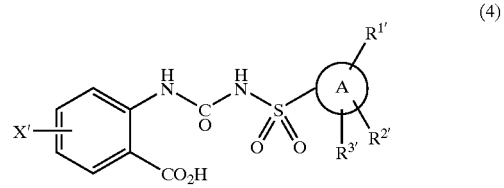

(4)

wherein the ring A, $R^{1'}$, $R^{2'}$, $R^{3'}$ and X' represent the same as defined above, then, a condensing agent for example, 1,1'-carbonyldiimidazole (hereinafter referred to as CDI) is used to obtain the quinazoline ring, and if necessary, the protecting groups of $R^1$, $R^2$, $R^3$ and X are deprotected.

In this reaction, when $R^1$, $R^2$ or $R^3$ represents a group containing a hydroxyl group, an amino group, or a carboxylic acid group, $R^1$, $R^2$ or $R^3$ may be optionally protected by a protecting group such as a benzyloxycarbonyl group, a t-butoxycarbonyl group, a benzyl group, an allyl group, a t-butyl group, etc. When X represents a hydroxyl group or an amino group, X may be optionally protected with a protecting group such as a benzyloxycarbonyl group, a t-butoxycarbonyl group, a benzyl group, an allyl group, a t-butyl group, etc.

The compound having the formula (2) used in this reaction includes a commercially available or known compound or a compound which can be synthesized by a known method may be used. For example, using the synthesis method described in the specification of European Patent No. 0269141, it is possible to use a compound which can be synthesized from the corresponding sulfonamide derivative using chlorosulfonyl isocyanate. For example, it is possible to use 3-allyloxycarbonyl-methylbenzenesulfonyl isocyanate, 4-allyloxycarbonyl-methylbenzenesulfonyl isocyanate, 4-allyloxybenzenesulfonyl isocyanate, etc.

As the anthranilic acid derivative having the formula (3) used for this reaction, a commercially available or known compound or a compound which can be synthesized by a known method may be used. For example, anthranilic acid, 4-chloroanthranilic acid, 4-methoxyanthranilic acid, 5-chloroanthranilic acid, 4-hydroxyanthranilic acid, etc. may be used.

The reaction to obtain the quinazoline ring from the sulfonylurea derivative having the formula (4) may be carried out using an aprotonic solvent such as, for example, an ether solvent such as tetrahydrofuran and dioxane, a halogen-containing solvent such as methylene chloride, or dimethylformamide etc. at a temperature of −50° C. to 50° C., preferably −20° C. to room temperature. Further, for the cyclization reaction, it is possible to use an ordinary condensing agent which includes, for example, CDI, dicyclohexylcarbodiimide, and similar carbodiimide compounds, mixed anhydrides, etc. The deprotecting reaction can be carried out by an ordinary method using hydrolysis with an acid or alkali, reduction or oxidation etc.

Synthesis Method (B)

A compound having the formula (5):

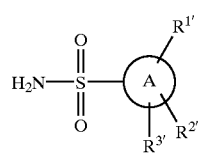

(5)

wherein the ring A, $R^{1'}$, $R^{2'}$ and $R^{3'}$ represent the same as defined above is condensed with an anthranilic acid derivative having the formula (6):

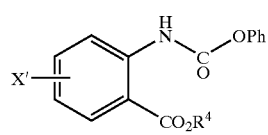

(6)

wherein X' represents the same as defined above, Ph represents a phenyl group, and $R^4$ represents a protecting group of the carboxyl group, which is specifically a group capable of being released by hydrolysis or hydrogenolysis, such as, for example, a methyl group, an ethyl group, or a benzyl group using, for example, 1,8-diazabicyclo[5,4,0]-7-undecene (hereinafter referred to as DBU) to form a sulfonylurea derivative having the formula (7):

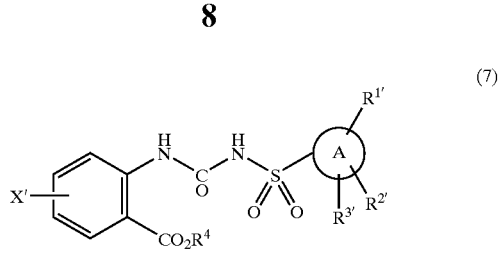

(7)

wherein the ring A, $R^{1'}$, $R^{2'}$, $R^{3'}$, $R^4$ and X' are the same as defined above, which is then hydrolyzed with an alkali or hydrogenolyzed to derive a corresponding carboxylic acid represented by the formula (4), then the quinazoline ring is obtained and optionally the protecting groups of $R^1$, $R^2$, $R^3$ and X are deprotected, in the same way as in Synthesis Method (A). In this reaction, when $R^1$, $R^2$ or $R^3$ represents a group containing a hydroxyl group, an amino group, or a carboxylic acid group, $R^1$, $R^2$ or $R^3$ may be optionally protected by a protecting group such as a benzyloxycarbonyl group, a t-butoxycarbonyl group, a benzyl group, an allyl group, a t-butyl group, etc. When X represents a hydroxyl group or an amino group, X may be optionally protected with a protecting group such as a benzyloxycarbonyl group, a t-butoxycarbonyl group, a benzyl group, an allyl group, a t-butyl group, etc.

As the compound having the formula (5) used in the reaction, a commercially available or known compound or a compound which can be synthesized by a known method may be used. For example, 3-hydroxybenzenesulfonamide, 2-aminobenzenesulfonamide, 3-aminobenzenesulfonamide, 4-aminobenzenesulfonamide, (±)-2-(4-aminosulfonylphenyl)butyric acid, 3-benzyloxycarbonylamino-4-chlorobenzenesulfonamide, 4-benzyloxycarbonylamino-3-chlorobenzenesulfonamide, 4-amino-3,5-dichlorobenzenesulfonamide, 3-benzyloxycarbonylamino-4-methylbenzenesulfonamide, 4-t-butoxycarbonyl-3-hydroxybenzenesulfonamide, 3-benzyloxycarbonylamino-4-t-butoxycarbonylbenzenesulfonamide, 4-t-butoxycarbonyl-3-hydroxybenzenesulfonamide, 3-t-butoxycarbonyl-4-hydroxybenzenesulfonamide, 3-acetamide-4-methoxybenzenesulfonamide, 3-(3-aminosulfonyl)phenylacrylic acid t-butylester, 3-amino-methoxybenzenesulfonamide, 4-methoxy-3-methylsulfonylaminobenzenesulfonamide, 3-carboxy-4-hydroxy-2-naphthalenesulfonamide, 4-benzyloxycarbonylamino-3-t-butoxycarbonylbenzenesulfonamide, (±)-3-t-butoxycarbonyl-2-oxo-1H,3H-quinoline-7-sulfonamide, (±)-2-t-butoxycarbonyl-3-oxo-1,4-benzoxazine-6-sulfonamide, etc. may be used.

As the anthranilic acid derivative having the formula (6) used in this reaction, a commercially available or known compound or a compound which can be synthesized by a known method may be used. For example, methyl 4-chloro-2-N-phenoxycarbonylanthranilate, ethyl 4-chloro-2-N-phenoxycarbonylanthranilate, benzyl 4-chloro-2-N-phenoxycarbonylanthranilate, methyl 5-chloro-2-N-phenoxycarbonylanthranilate, ethyl 5-chloro-2-N-phenoxycarbonylanthranilate, benzyl 5-chloro-2-N-phenoxycarbonylanthranilate, methyl 4-methoxy-2-N-phenoxycarbonylanthranilate, ethyl 4-methoxy-2-N-phenoxycarbonylanthranilate, benzyl 4-methoxy-2-N-phenoxycarbonylanthranilate, methyl 4-hydroxy-2-N- phenoxycarbonylanthranilate, ethyl 4-hydroxy-2-N-phenoxycarbonylanthranilate, benzyl 4-hydroxy-2-N-phenoxycarbonylanthranilate, etc. may be used.

The reaction for obtaining the compound having the formula (5) and the anthranilic acid derivative having the formula (6) condense to obtain a sulfonylurea derivative having the formula (7), may be carried out using an aprotic solvent, for example, an ether solvent such as tetrahydrofuran or dioxane, a halogen-containing solvent such as methylene chloride, or dimethylformamide etc. at a temperature of −50° C. to 50° C., preferably −20° C. to room temperature. Further, as the usable for the condensation reaction, an organic strong base such as DBU, inorganic bases such as potassium carbonate, sodium carbonate, potassium hydroxide, and sodium hydroxide, or metal bases such as sodium hydride may be used.

In the reaction for alkali hydrolysis or hydrogenolysis of the sulfonylurea derivative having the formula (7) thus obtained to obtain the sulfonylurea derivative having the formula (4), ordinary hydrolysis conditions or hydrogenolysis conditions for esters may be used.

Note that the above reaction may be carried out while protecting the functional groups not involved in the reaction. According to the type of the protecting group, the protection is removed by chemical reduction or other ordinary protection-removing reactions. For example, when the protecting group is a t-butyl group or t-butoxycarbonyl group, trifluoroacetic acid may be used, while when it is an allyl group, palladium catalysts such as tetrakis(triphenylphosphine)palladium (0) may be used.

The compound having the formula (1), wherein $R^1$ represents an amino group acylated with a $C_1$ to $C_4$ lower aliphatic acid which may be substituted with a carboxylic acid, an amino group acylated with an aromatic ring carboxylic acid which may be substituted with a carboxylic acid and an amino group acylated with an heteroaromatic ring carboxylic acid which may be substituted with a carboxylic acid, can be obtained from the compound having the formula (1), wherein $R^1$ represents an amino group, by acylating the same with carboxylic acid, carboxylic acid chloride, carboxylic acid anhydride using an ordinary method.

The compound having the formula (1), wherein $R^1$ represents an amino group sulfonylated with a $C_1$ to $C_4$ lower alkane sulfonic acid which may be substituted with a carboxylic acid, an amino group sulfonylated with an aromatic ring sulfonic acid which may be substituted with a carboxylic acid and an amino group sulfonylated with an heteroaromatic ring sulfonic acid which may be substituted with a carboxylic acid, can be obtained from the compound having the formula (1), wherein $R^1$ represents an amino group, by sulfonylating the same with sulfonic acid or sulfonic acid chloride using an ordinary method.

The product obtained according to the above-mentioned processes can be purified by a method such as recrystallization or column chromatography.

If necessary, the compounds having the formula (1) of the present invention obtained according to the above-mentioned processes can each be reacted with one of various acids or basis to convert the compound into their salt. Exemplary acids usable for the conversion of the compound having the formula (1) into their salts can include inorganic acids such as hydrochloric acid, hydrobromic acid, nitric acid, sulfuric acid, phosphoric acid; and organic acids such as methanesulfonic acid, benzenesulfonic acid, p-toluenesulfonic acid, trifluoroacetic acid, citric acid, lactic acid, maleic acid, fumaric acid, tartaric acid, acetic acid, adipic acid, palmitic acid and tannic acid. Exemplary usable basis for the conversion of the compound having the formula (1) into their salts can include sodium hydroxide, lithium hydroxide and potassium hydroxide.

Further, the compounds having the formula (1) according to the present invention include those containing asymmetric centers. Each racemic mixture can be isolated by one or more of various methods, whereby a single optically-active substance can be obtained. Usable methods include, for example:

(1) Isolation by optically active column.
(2) Isolation by recrystallization subsequent to conversion into a salt with an optically active acid or base.
(3) Isolation by a combination of the above methods (1) and (2).

The quinazoline derivative of the present invention has an inhibitory activity with respect to human chymase. Further, it suppresses the exacerbation of vascular permeability caused by chymase. Further, it exhibits a sufficient half-life in human plasma. Therefore, as an inhibitor for mast cell chymase including human chymase, it is expected to be useful as a medicament for the prevention or treatment of cardiac and circulatory system diseases due to abnormal production of Ang II and for the prevention or treatment of allergic diseases and rheumatoid arthritis.

To use the effective ingredient of the present invention as a pharmaceutical composition for the prevention or treatment of cardiac and circulatory system diseases due to the abnormal exacerbation of Ang II production and allergic diseases and rheumatic diseases which are related to mast cells, one or more of the compounds of the present invention may be mixed and formed into a form suitable for use in the method of administration by an ordinary method. Examples of preparation forms for oral administration include capsules, tablets, granules, fine granules, syrups, dry syrups, and other preparations, while examples of preparation forms for non-oral administration include injections and besides suppositories such as rectal suppositories and vaginal suppositories, transnasal preparations such as sprays and ointments, and percutaneous preparations such as tapes for percutaneous absorption.

The clinical dose of the compound according to the present invention varies according to the diseased condition, degree of seriousness, age, presence of complications, etc. and also varies according to its preparation form. In the case of oral administration, however, it may be dosed usually, in terms of effective ingredients, as 1 to 1000 mg per adult per day. In the case of non-oral administration, it is sufficient to administer 1/10 to 1/2 the amount of the case of oral administration. These dosages can be suitably adjusted according to the age, the diseased condition, and the like of the patient to be dosed.

The toxicity of the compound according to the present invention is low. The acute toxicity values $LD_{50}$ at 24 hours after oral administration to 5-week old male mice were 1 g/kg or more.

EXAMPLES

The present invention will now be further explained by, but is by no means limited to, the following Examples, but the scope of the invention is not limited to these Examples needless to say.

Example 1

Synthesis of 7-chloro-3-(3-hydroxybenzenesulfonyl)-2,4(1H,3H)-quinazolinedione (Compound 1)

Following the Synthesis Method (B), 938 mg (5.42 mmol) of 3-hydroxybenzenesulfonamide was dissolved in 40 ml of tetrahydrofuran, then 892 µl (5.96 mmol) of 1,8-diazabicyclo[5,4,0]-7-undecene (hereinafter referred to as DBU) was added dropwise. The reaction solution was stirred at room temperature for 15 minutes, then 1.66 g (5.42 mmol) of methyl 4-chloro-2-N-phenoxycarbonylanthranilate was added and the mixture was stirred at room temperature overnight. An excess amount of water was poured into the reaction solution, then the mixture was made acidic with hydrochloric acid and extracted with ethyl acetate. The organic layer was washed with water and saturated saline, dried over anhydrous magnesium sulfate, and concentrated. The crude product thus obtained was purified by silica gel column chromatography (0% to 5% methanol/dichloromethane) to obtain 1.23 g (yield 59%) of methyl 4-chloro-2-{([(3-hydroxybenzenesulfonylamino)carbonyl]amino} benzoate. Properties: colorless amorphous, PMR (δ ppm, DMSO-$d_6$): 3.91 (3H, s), 7.02 (1H, m), 7.09 (1H, m), 7.34 (1H, t), 7.57 (2H, m), 7.89 (1H, d), 8.38 (1H, d), 10.94 (1H, s). Next, the 1.23 g (3.2 mmol) of the compound thus obtained was dissolved in 20 ml of methanol, then 10 ml of 2N sodium hydroxide aqueous solution was added dropwise. The reaction solution was stirred at room temperature for 15 minutes, then an excess amount of water was added and the mixture was made acidic with hydrochloric acid. This was then stirred to cause crystals to precipitate which were then obtained by filtration and dried to obtain carboxylic acid. The product thus obtained was dissolved in 50 ml of tetrahydrofuran (hereinafter referred to as THF), then 434 mg (2.68 mmol) of CDI was added under ice cooling and the mixture was stirred for 30 minutes. The reaction solution was diluted with ethyl acetate, washed with water and saturated saline, and dried over anhydrous magnesium sulfate, then concentrated to obtain a crude product. The crude product was purified by silica gel column chromatography (ethyl acetate:n-hexane=1:2) to obtain 230 mg (yield 20%: 2 steps) of the above-identified compound. Properties: colorless crystal, Melting point: >200° C. (decomposition), PMR (δ ppm, DMSO-$d_6$): 7.12 (2H, s), 7.24 (1H, d), 7.48 (1H, t), 7.58 (2H, s), 7.85 (1H, d), 10.28 (1H, s), 11.63 (1H, s).

Example 2

Synthesis of 3-(2-aminobenzenesulfonyl)-7-chloro-2,4(1H,3H-quinazolinedione (Compound 2)

2.7 g (15.7 mmol) of 2-aminobenzenesulfonamide and 4.8 g (15.7 mmol) of methyl 4-chloro-2-N-phenoxycarbonylanthranilate were treated in the same way as Example 1 to obtain 3.2 g (yield 58%: 3 steps) of the above-identified compound. Properties: colorless crystal, Melting point: >200° C. (decomposition), PMR (δ ppm, DMSO-$d_6$): 6.46 (2H, s), 6.65 (1H, t), 6.81 (1H, d), 7.12 (1H, s), 7.23 (1H, d), 7.34 (1H, t), 7.76 (1H, d), 7.86 (1H, d).

Example 3

Synthesis of 7-chloro-3-(2-methylsulfonylaminobenzenesulfonyl)-2,4(1H,3H)-quinazolinedione (Compound 3)

22 mg (0.06 mmol) of Compound 2 was dissolved in 200 µl of pyridine, 11.6 µl (0.15 mmol) of methanesulfonyl chloride was added dropwise, then the resultant mixture was stirred at room temperature overnight. An excess amount of water was added to the reaction solution and the mixture was extracted with ethyl acetate. The organic layer was washed with 1N aqueous hydrochloric acid solution and saturated saline, then dried over anhydrous magnesium sulfate and concentrated to obtain a crude product. The crude product was crystallized from diethyl ether to obtain 16 mg (0.04 mmol) of the above-identified compound. Properties: colorless crystal, Melting point: >200° C. (decomposition), PMR (δ ppm, DMSO-$d_6$): 3.61 (3H, s), 7.10 (1H, d), 7.20 (1H, d), 7.74 (1H, d), 7.82–7.90 (4H, m), 8.34 (1H, d), 11.70 (1H, 9).

Example 4

Synthesis of 3-(4-aminobenzenesulfonyl)-7-chloro-2,4(1H,3H)-quinazolinedione (Compound 4)

2.7 g (15.7 mmol) of 4-aminobenzenesulfonamide and 4.8 g (15.7 mmol) of methyl 4-chloro-2-N-phenoxycarbonylanthranilate were treated in the same way as Example 1 to obtain 7.9 g (yield 94%) of methyl 2-{[(4-aminobenzenesulfonylamino)carbonyl]amino}-4-chlorobenzoate. Properties: colorless amorphous, PMR (δ ppm, DMSO-$d_6$): 3.59 (3H, s), 5.37 (2H, s), 6.45 (2H, d), 6.83 (1H, dd), 7.41 (2H, d), 7.81 (1H, d), 8.66 (1H, d), 9.64 (1H, s).

Then, from the resultant 7.9 g (14.8 mmol) of sulfonylurea product, in the same way, 4.3 g (yield 83%: 2 steps) of the above-identified compound was obtained. Properties: colorless crystal, Melting point: >200° C. (decomposition), PMR (δ ppm, DMSO-$d_6$); 2.33 (3H, s), 6.93 (1H, m), 7.13 (1H, d), 7.23–7.26 (3H, m), 7.30 (1H, s), 7.86 (1H, d), 11.61 (1H, s).

Example 5

Synthesis of 3-(3-carboxymethyl-benzenesulfonyl)-7-chloro-2,4(1H,3H)-quinazolinedione (Compound 5)

Following the Synthesis Method (A), 3.27 g (11.6 mmol) of 3-allyloxycarbonylmethylbenzenesulfonyl isocyanate was dissolved in 100 ml of anhydrous THF, then 1.98 g (11.5 mmol) of 4-chloroanthranilic acid was added and the mixture was stirred at room temperature for 2 hours. The reaction solution was cooled with ice water, then 1.87 g (11.5 mmol) of CDI was added and the resultant mixture was stirred under ice cooling for 30 minutes. An excess amount of water was poured into the reaction solution, then the mixture was extracted with ethyl acetate. The organic layer was washed, dried, and concentrated to obtain a crude product. This was crystallized with a small amount of ethyl acetate to obtain 2.0 g (yield 40%) of 3-(3-allyloxycarbonylmethylbenzenesulfonyl)-7-chloro-2,4(1H,3H)-quinazolinedione. The allyl product thus obtained was dissolved in 100 ml of a formic acid-THF (1:9) mixture and 700 mg of triphenylphosphine was added. The reactor was shaded from light and under nitrogen atmosphere, then 700 mg of tetrakis(triphenylphosphine)palladium (0) was added and the resultant mixture was stirred while shaded at room temperature overnight. The reaction solution was concentrated in vacuo and the solid obtained was washed with methylene chloride to obtain 1.47 g (yield 81%) of the above-identified compound. Properties: colorless crystal, Melting point: >200° C. (decomposition), PMR (δ ppm, DMSO-$d_6$): 3.76 (2H, s), 7.13 (1H, s), 7.24 (1H, d), 7.61–7.69 (2H, m), 7.86 (1H, d), 8.05 (2H, s), 12.50 (1H, br).

Example 6

Synthesis of 3-(4-carboxymethyl-benzenesulfonyl)-7-chloro-2,4(1H,3H)-quinazolinedione (Compound 6)

1.10 g (3.95 mmol) of 4-allyloxycarbonylmethylbenzenesulfonyl isocyanate and 678 mg (3.95 mmol) of 4-chloroanthranilic acid were treated in the same way as in Example 5 to obtain 657 mg (yield 38%) of 3-(4-allyloxycarbonylbenzenesulfonyl)-7-chloro-2,4(1H,3H)-quinazolinedione. 538 mg (1.24 mmol) thereof was treated in the same way to obtain 342 mg of the above-identified compound (yield 70%). Properties: colorless crystal, Melting point: >200° C. (decomposition), PMR (δ ppm, DMSO-d$_6$): 3.75 (2H, s), 7.13 (1H, s), 7.23 (1H, d), 7.61–7.69 (2H, m), 7.86 (1H, d), 8.05 (2H, s), 12.07 (2H, br).

Example 7

Synthesis of (±)-2-{4-[(7-chloro-2,4(1H,3H)-quinazolin-3-yl)sulfonyl]phenyl}butyric acid (Compound 7)

1.02 g (3.41 mmol) of t-butyl(±)-2-(4-aminosulfonylphenyl)butyrate acid and 1.04 g (3.41 mmol) of methyl 4-chloro-2-N-phenoxycarbonylanthranilate were treated in the same way as Example 1 to obtain 1.46 g (yield 84%) of methyl 2-[({4-[1-(t-butoxycarbonyl)propyl]benzenesulfonylamino}carbonyl)amino]-4-chlorobenzoate. Properties: colorless amorphous, PMR (δ ppm, CDCl$_3$):0.89 (3H, t), 1.38 (9H, s), 1.69–1.76 (1H, m), 2.03–2.10 (1H, m), 3.42 (1H, t), 3.94 (3H, s), 7.04 (1H, d), 7.47 (2H, d), 7.93 (1H, d), 8.01 (2H, d), 8.45 (1H, br), 11.04 (1H, br).

Next, 4.3 ml (8.6 mmol) of 2N sodium hydroxide aqueous solution was used to similarly form carboxylic acid in an amount of 1.43 g and 463 mg (2.86 mmol) of CDI was used to obtain 970 mg (yield 71%: 2 steps) of t-butyl(±)-2-{4-[(7-chloro-2,4(1H,3H)-quinazolin-3-yl)sulfonyl]phenyl}butyrate.

Further, the t-butylester thus obtained was dissolved in 5 ml of dichloromethane, then 5 ml of trifluoroacetic acid was added and the resultant mixture was stirred at room temperature for 40 minutes. The reaction solution was concentrated in vacuo and the resultant crude product was washed with a small amount of diethyl ether to obtain 820 mg of the above-identified compound (yield 96%). Properties: colorless crystal, Melting point: >200° C. (decomposition), PMR (δ ppm, DMSO-d$_6$): 0.84 (3H, t), 1.67–1.75 (1H, it), 1.98–2.05 (1H, m), 3.62 (1H, t), 7.11 (1H, s), 7.24 (1H, d), 7.61 (2H, d), 7.86 (1H, d), 8.13 (2H, d), 11.62 (1H, s).

Example 8

Synthesis of 3-(3-amino-4-chlorobenzenesulfonyl)-7-chloro-2,4(1H,3H)-quinazolinedione (Compound 8)

1.0 g (2.93 mmol) of 3-benzyloxycarbonylamino-4-chlorobenzenesulfonamide and 1.18 g (2.93 mmol) of benzyl 4-chloro-2-N-phenoxycarbonylanthranilate were treated in the same way as Example 1 to obtain 1.43 g (yield 78%) of benzyl 2-{[(3-benzyloxycarbonylamino-4-chlorobenzenesulfonylamino)carbonyl]amino}-4-chlorobenzoate. Properties: colorless amorphous, PMR (δ ppm, DMSO-d$_6$): 5.19 (2H, s), 5.36 (2H, s), 7.21 (1H, dd), 7.34–7.48 (10H, m), 7.72–7.76 (2H, m), 7.97 (1H, d), 8.25 (1H, d), 8.30 (1H, d), 9.53 (1H, s), 10.30 (1H, s). 1.38 g (2.20 mmol) thereof was dissolved in 50 ml of THF, then 200 mg of palladium-carbon (10%) was added and the mixture was stirred under a hydrogen flow for 2 hours. The reaction mixture was filtered with Celite to remove the palladium-carbon, then the filtrate was concentrated in vacuo to obtain a carboxylic acid. The product obtained was suspended in 50 ml of THF, then 356 mg (2.20 mmol) of CDI was added under ice cooling and the resultant mixture was treated in the same way as Example 1 to obtain 560 mg (yield 66%: 2 steps) of the above-identified compound. Properties: colorless crystal, Melting point: >200° C. (decomposition), PMR (δ ppm, DMSO-d$_6$): 6.00 (2H, s), 7.12 (1H, s), 7.26 (2H, t), 7.48 (1H, d), 7.66 (1H, s), 7.86 (1H, d), 11.76 (1H, br).

Example 9

Synthesis of 3-(4-amino-3.5-dichlorobenzenesulfonyl)-7-chloro-2,4(1H,3H)-quinazolinedione (Compound 9)

1.06 g (4.40 mmol) of 4-amino-3,5-dichlorobenzenesulfonamide and 1.34 g (4.40 mmol) of methyl 4-chloro-2-N-phenoxycarbonylanthranilate were treated in the same way as Example 1 to obtain 905 mg (yield 44%) of methyl 2-{[(4-amino-3,5-dichlorobenzenesulfonylamino)carbonyl]amino}-4-chlorobenzoate. Properties: colorless amorphous, PMR (δ ppm, DMSO-d$_6$): 3.87 (3H, s), 6.59 (2H, br), 7.22 (1H, dd), 7.72 (2H, s), 7.93 (1H, d), 8.24 (1H, d), 10.17 (1H, s).

Then, from 905 mg (2.0 mmol) of the resultant sulfonylurea product, in the same way, 660 mg (yield 82%: 2 steps) of the above-identified compound was obtained. Properties: colorless crystal, Melting point: >200° C. (decomposition), PMR (δ ppm, DMSO-d$_6$): 6.80 (2H, s), 7.12 (1H, s), 7.24 (1H, d), 7.86 (1H, d), 7.92 (2H, s), 11.63 (1H, br).

Example 10

Synthesis of 3-(3-amino-4-methylbenzenesulfonyl)-7-chloro-2,4(1H,3H)-quinazolinedione (Compound 10)

960 mg (3.00 mmol) of 3-benzyloxycarbonylamino-4-methylbenzenesulfonamide and 1.14 g (3.00 mmol) of benzyl 4-chloro-2-N-phenoxycarbonylanthranilate were treated in the same way as in Example 8 to obtain 1.14 g (yield 62% of benzyl 2-{[(3-benzyloxycarbonylamino-4-methylbenzenesulfonylamino)carbonyl]amino}-4-chlorobenzoate. Properties: colorless amorphous, PMR (δ ppm, DMSO-d$_6$): 2.30 (3H, s), 5.17 (2H, s), 5.36 (2H, s), 7.20 (1H, dd), 7.33–7.48 (1H, m), 7.63 (1H, d), 7.97 (1H, d), 8.11 (1H, s), 8.25 (1H, s), 9.27 (1H, s), 10.30 (1H, s), 12.20 (1H, br).

Then, from 1.14 g (1.87 mmol) of the resultant sulfonylurea product, in the same way, 190 mg (yield 27%: 2 steps) of the above-identified compound was obtained. Properties: colorless crystal, Melting point: >200° C. (decomposition), PMR (δ ppm, DMSO-d$_6$): 2.12 (3H, s), 5.47 (2H, s), 7.12 (1H, s), 7.16–7.25 (3H, m), 7.38 (1H, s), 7.85 (1H, d), 11.58 (1H, s).

Example 11

Synthesis of 3-[(3-carboxymethylaminophenyl)sulfonyl]-7-chloro-2,4(1H,3H)-quinazolinedione (Compound 11)

1.62 g (5.65 mmol) of 3-t-butoxycarbonylmethylaminobenzenesulfonamide and 1.73 g (5.65 mmol) of methyl 4-chloro-2-N-phenoxycarbonylanthranilate were treated in the same way as in Example 7 to obtain 209 mg (yield 9%: 4 steps) of the above-identified compound. Properties: colorless crystal, Melting point: >200° C. (decomposition), PMR (δ ppm, DMSO-d$_6$): 3.86 (2H, s), 6.88 (1H, s), 7.12 (1H, s), 7.24 (1H, d), 7.30–7.38 (3H, m), 7.86 (1H, d), 11.61 (1H, br).

Example 12

Synthesis of 3-(3-aminobenzenesulfonyl)-7-chloro-2,4(1H,3H)-quinazolinedione (Compound 12)

3.5 g (12.9 mmol) of 3-t-butoxycarbonylaminobenzenesulfonamide and 3.9 g (12.8 mmol) of methyl 4-chloro-2-N-phenoxycarbonylanthranilate were treated in the same way as in Example 7 to obtain 2.2 g (yield 49%: 4 steps) of the above-identified compound. Properties: colorless crystal, Melting point: >200° C. (decomposition), PMR (δ ppm, DMSO-$d_6$): 5.72 (2H, s), 6.87 (1H, d), 7.12 (1H, s), 7.23–7.27 (2H, m), 7.33 (1H, s), 7.86 (1H, d), 11.61 (1H, s).

Example 13

Synthesis of 2-{3-[(7-chloro-2,4(1H,3H)-quinazolinedion-3-yl)sulfonyl]phenylaminocarbonyl}propionic acid (Compound 13)

100 mg (0.28 mmol) of Compound 12 was dissolved in 5 ml of THF, 100 mg (1.0 mmol) of succinic anhydride was added, and the resultant mixture was heated and refluxed for 3 hours. The reaction solution was concentrated in vacuo and the crude product thus obtained was crystallized with ethyl acetate-diethyl ether to obtain 120 mg (yield 96%) of the above-identified compound. Properties: colorless crystal, Melting point: 187–188° C., PMR (δ ppm, DMSO-$d_6$): 2.54 (2H, d), 2.59 (2H, d), 7.12 (1H, s), 7.24 (1H, d), 7.59 (1H, t), 7.80 (1H, d), 7.86 (1H, d), 7.96 (1H, d), 8.41 (1H, s), 10.40 (1H, s), 11.63 (1H, br), 12.10 (1H, br).

Example 14

Synthesis of 3-{3-[(7-chloro-2,4(1H,3H)-quinazolinedion-3-yl)sulfonyl]phenyl}acrylic acid (Compound 14)

1.54 g (5.44 mmol) of t-butyl 3-(3-aminosulfonyl)phenylacrylate and 1.66 g (5.44 mmol) of methyl 4-chloro-2-N-phenoxycarbonylanthranilate were treated in the same way as in Example 7 to obtain 2.18 g (yield 81%) of methyl 2-({[3-(3-t-butoxy-3-oxo-1-propenyl)benzenesulfonylamino]carbonyl}amino)-4-chlorobenzoate. Properties: colorless amorphous, PMR (δ ppm, CDCl$_3$): 1.53 (9H, s), 3.95 (3H, s), 6.46 (1H, d), 7.05 (1H, d), 7.55 (1H, m), 7.57 (1H, d), 7.72 (1H, m), 7.93 (1H, m), 8.04 (1H, m), 8.27 (1H, s), 8.46 (1H, d), 11.05 (1H, br).

Then, from 2.18 g (4.4 mmol) of the resultant sulfonylurea product, in the same way, 698 mg (yield 37%: 3 steps) of the above-identified compound was obtained. Properties: colorless crystal, Melting point: >200° C. (decomposition), PMR (δ ppm, DMSO-$d_6$): 6.65 (1H, d), 7.12 (1H, s), 7.25 (1H, d), 7.69 (1H, d), 7.72 (1H, t), 7.87 (1H, d), 8.12 (2H, q), 8.37 (1H, s), 11.64 (1H, s).

Example 15

Synthesis of 4-[(7-chloro-2,4(1H,3H)-quinazolinedion-3-yl)sulfonyl]salicylic acid (Compound 15)

1.0 g (3.66 mmol) of 4-t-butoxycarbonyl-3-hydroxybenzenesulfonamide and 1.12 g (3.66 mmol) of methyl 4-chloro-2-N-phenoxycarbonylanthranilate were treated in the same way as in Example 7 to obtain 1.79 g (yield 100%) of methyl 2-{[(4-t-butoxycarbonyl-3-hydroxybenzenesulfonylamino)carbonyl]amino}-4-chlorobenzoate. Properties: colorless amorphous, PMR (δ ppm, DMSO-$d_6$): 1.57 (9H, s), 3.87 (3H, s), 7.14 (1H, d), 7.40–7.45 (2H, m), 7.85 (1H, d), 7.92 (1H, d), 8.32 (1H, d), 10.13 (1H, s), 10.82 (1H, s).

Then, from 1.78 g (3.66 mmol) of the resultant sulfonylurea product, in the same way, 370 mg (yield 25%: 3 steps) of the above-identified compound was obtained. Properties: colorless crystal, Melting point: >200° C. (decomposition), PMR (δ ppm, DMSO-$d_6$): 7.13 (1H, s), 7.26 (1H, d), 7.69 (1H, d), 7.87 (1H, d), 8.01 (1H, d), 11.67 (1H, s).

Example 16

Synthesis of 4-[(7-chloro-2,4(1H,3H)-quinazolinedion-3-yl)sulfonyl]salicylic acid monosodium salt (Compound 16)

50 mg (0.13 mmol) of Compound 15 was suspended in approximately 1 ml of THF, then 126 μl of 1N sodium hydroxide aqueous solution was added dropwise. The solution was confirmed to have become uniform, then 30 ml of water was added and the mixture freeze-dried to quantitatively obtain the above-identified compound in an amorphous state in an amount of 52 mg. Properties: colorless amorphous, PMR (δ ppm, CD$_3$OD): 7.11 (1H, s), 7.19 (1H, d), 7.58 (1H, d), 7.63 (1H, s), 7.92 (1H, d), 8.03 (1H, d).

Example 17

Synthesis of 4-[(7-chloro-2,4(1H,3H)-quinazolinedion-3-yl)sulfonyl]anthranilic acid (Compound 17)

2.84 g (6.99 mmol) of 3-benzyloxycarbonylamino-4-t-butoxycarbonylbenzenesulfonamide and 2.67 g (6.99 mmol) of benzyl 4-chloro-2-N-phenoxycarbonylanthranilate were treated in the same way as in Example 8 to obtain 3.74 g (yield 77%) of benzyl 2-{[(3-benzyloxycarbonylamino-4-t-butoxycarbonylbenzenesulfonylamino)carbonyl]amino}-4-chlorobenzoate. Properties: colorless amorphous, PMR (δ ppm, DMSO-$d_6$): 1.54 (9H, s), 5.19 (2H, s), 5.34 (2H, s), 7.05 (1H, m), 7.34–7.58 (10H, m), 7.60 (1H, d), 7.90 (1H, d), 7.98 (1H, d), 8.50 (1H, br), 8.62 (1H, s), 10.00 (1H, br), 10.41 (1H, s).

Then, from 3.74 g (5.39 mmol) of the resultant sulfonylurea, in the same way, 690 mg (yield 30%: 2 steps) of t-butyl 4-[(7-chloro-2,4(1H,3H)-quinazolinedion-3-yl)sulfonyl]anthranilate was obtained, then this was subjected to a similar debutylation reaction to obtain 503 mg (yield 84%) of the above-identified compound. Properties: colorless crystal, Melting point: >200° C. (decomposition), PMR (δ ppm, DMSO-$d_6$): 7.14 (1H, s), 7.18 (1H, d), 7.25 (1H, d), 7.59 (1H, s), 7.87 (1H, d), 7.89 (1H, d), 11.62 (1H, s).

Example 18

Synthesis of 4-[(7-chloro-2,4(1H,3H)-quinazolinedion-3-yl)sulfonyl]anthranilic acid monosodium salt (Compound 18)

50 mg (0.13 mmol) of Compound 17 was suspended in approximately 1 ml of THF, then 126 μl of 1N sodium hydroxide aqueous solution was added dropwise. The solution was confirmed to have become uniform, then 30 ml of water was added and the mixture was freeze-dried to quantitatively obtain the above-identified compound in an amorphous state in an amount of 52 mg. Properties: colorless amorphous, PMR (δ ppm, DMSO-$d_6$): 7.11–7.22 (3H, m), 7.37 (1H, s), 7.83 (1H, d), 7.91 (1H, d).

Example 19

Synthesis of 3-(4-hydroxybenzenesulfonyl)-7-chloro-2,4(1H,3H)-quinazolinedione (Compound 19)

1.50 g (7.03 mmol) of 4-allyloxybenzenesulfonyl isocyanate and 1.2 g (7.03 mmol) of 4-chloroanthranilic acid were treated in the same way as in Example 5 to obtain 1.5 g (yield 53%) of 3-(4-allyloxybenzenesulfonyl)-7-chloro-2,4 (1H,3H)-quinazolinedione. 500 mg (1.27 mmol) thereof was similarly treated to obtain 405 mg of the above-identified compound (yield 90%). Properties: colorless crystal, Melting point: >200° C. (decomposition), PMR (δ ppm, DMSO-$d_6$): 6.98 (2H, d), 7.11 (1H, s), 7.23 (1H, d), 7.85 (1H, d), 8.00 (2H, d), 11.25 (1H, br).

Example 20

Synthesis of 4-[(2,4(1H,3H)-quinazolinedion-3-yl) sulfonyl]salicylic acid (Compound 20)

618 mg (2.26 mmol) of 4-t-butoxycarbonyl-3-hydroxybenzenesulfonamide and 613 mg (2.26 mmol) of methyl 2-N-phenoxycarbonylanthranilate were treated in the same way as in Example 17 to obtain 792 mg (yield 78%) of methyl 2-{[(4-t-butoxycarbonyl-3-hydroxybenzenesulfonylamino)carbonyl]amino}benzoate. Properties: colorless amorphous, PMR (δ ppm, $CDCl_3$): 1.60 (9H, s), 3.97 (3H, s), 7.09 (1H, t), 7.49–7.52 (2H, m), 7.65 (1H, d), 7.90 (1H, d), 8.01 (1H, dd), 8.33 (1H, d), 10.98 (1H, s), 11.18 (1H, s).

Then, from 790 mg (1.75 mmol) of the resultant sulfonylurea product, in the same way, 100 mg (yield 8%: 3 steps) of the above-identified compound was obtained. Properties: colorless crystal, Melting point: >200° C. (decomposition), PMR (δ ppm, DMSO-$d_6$): 7.13 (1H, d), 7.22 (1H, t), 7.63–7.69 (3H, m), 7.87 (1H, d), 8.01 (1H, d), 11.57 (1H, s).

Example 21

Synthesis of 5-[7-chloro-2,4(1H,3H)-quinazolinedion-3-yl)sulfonyl]salicylic acid (Compound 21)

320 mg (1.17 mmol) of 3-t-butoxycarbonyl-4-hydroxybenzenesulfonamide and 447 mg (1.17 mmol) of benzyl 4-chloro-2-N-phenoxycarbonylanthranilate were treated in the same way as in Example 17 to obtain 611 mg (yield 93%) of benzyl 2-{[(3-t-butoxycarbonyl-4-hydroxybenzenesulfonylamino)carbonyl]amino}-4-chlorobenzoate. Properties: colorless amorphous, PMR (δ ppm, $CDCl_3$): 1.62 (9H, s), 5.35 (2H, s), 7.01–7.05 (2H, m), 7.37–7.41 (5H, m), 7.96 (1H, d), 8.10 (1H, dd), 8.46–8.48 (2H, m), 10.99 (1H, s), 11.66 (1H, s).

Then, from 611 mg (1.09 mmol) of the resultant sulfonylurea product, in the same way, 114 mg (yield 33%: 3 steps) of the above-identified compound was obtained. Properties: colorless crystal, Melting point: >200° C. (decomposition), PMR (δ ppm, DMSO-$d_6$): 7.11 (1H, s), 7.19 (1H, d), 7.24 (1H, d), 7.86 (1H, d), 8.20 (1H, d), 8.56 (1H, s), 11.57 (1H, s).

Example 22

Synthesis of 3-(3-acetamide-4-methoxybenzenesulfonyl)-7-chloro-2,4(1H,3H)-quinazolinedione (Compound 22)

500 mg (2.19 mmol) of 3-acetamide-4-methoxybenzenesulfonamide and 836 mg (2.19 mmol) of benzyl 4-chloro-2-N-phenoxycarbonylanthranilate were treated in the same way as in Example 8 to obtain 812 mg (yield 70%) of benzyl 2-{[(3-acetylamino-4-methoxybenzenesulfonylamino)carbonyl]amino}-4-chlorobenzoate. Properties: colorless amorphous, PMR (δ ppm, DMSO-$d_6$): 2.12 (3H, s), 3.93 (3H, s), 5.36 (2H, s), 7.20 (1H, d), 7.24 (1H, d), 7.36–7.48 (5H, m), 7.69 (1H, d), 7.96 (1H, d), 8.24 (1H, s), 8.67 (1H, s), 9.39 (1H, s), 10.25 (1H, s), 12.11 (1H, br).

Then, from 611 mg (1.09 mmol) of the resultant sulfonylurea product, in the same way, 250 mg (yield 39%: 2 steps) of the above-identified compound was obtained. Properties: colorless crystal, Melting point: >200° C. (decomposition), PMR (δ ppm, DMSO-$d_6$): 2.12 (3H, s), 3.95 (3H, s), 7.12 (1H, s), 7.23 (1H, d), 7.30 (1H, d), 7.85 (1H, d), 7.89 (1H, d), 8.80 (1H, s), 9.42 (1H, s), 11.59 (1H, br).

Example 23

Synthesis of 3-(3-amino-4-methoxybenzenesulfonyl)-7-chloro-2,4(1H,3H)-quinazolinedione (Compound 23)

400 mg (1.40 mmol) of 3-t-butoxycarbonylamino-4-methoxybenzenesulfonamide and 533 mg (1.40 mmol) of benzyl 4-chloro-2-N-phenoxycarbonylanthranilate were treated in the same way as in Example 17 to obtain 86 mg (yield 16%: 4 steps) of the above-identified compound. Properties: colorless crystal, Melting point: >200° C. (decomposition), PMR (δ ppm, DMSO-$d_6$): 3.81 (3H, s), 7.26–7.37 (5H, m), 7.77 (1H, s), 7.90 (1H, d), 7.94 (1H, d), 11.73 (1H, s).

Example 24

Synthesis of 7-chloro-3-(4-methoxy-3-methylsulfonylaminobenzenesulfonyl)-2,4(1H,3H)-quinazolinedione (Compound 24)

500 mg (1.89 mmol) of 4-methoxy-3-methylsulfonylaminobenzenesulfonamide and 722 mg (1.89 mmol) of benzyl 4-chloro-2-N-phenoxycarbonylanthranilate were treated in the same way as in Example 8 to obtain 888 mg (yield 83%) of benzyl 2-({[(4-methoxy-3-methylsulfonylamino)benzene sulfonylamino]carbonyl}amino)-4-chlorobenzoate. Properties: colorless amorphous, PMR (δ ppm, DMSO-$d_6$): 2.12 (3H, s), 3.93 (3H, s), 5.36 (2H, s), 7.20 (1H, d), 7.24 (1H, d), 7.36–7.48 (5H, m), 7.69 (1H, d), 7.96 (1H, d), 8.24 (1H, s), 8.67 (1H, s), 9.39 (1H, s), 10.25 (1H, s), 12.11 (1H, br).

Then, from 880 mg (1.55 mmol) of the resultant sulfonylurea product, in the same way, 620 mg (yield 85%: 2 steps) of the above-identified compound was obtained. Properties: colorless crystal, Melting point: >200° C. C3 (decomposition), PMR (δ ppm, DMSO-$d_6$): 3.04 (3H, s), 3.94 (3H, s), 7.11 (1H, s), 7.23 (1H, d), 7.34 (1H, d), 7.86 (1H, d), 7.99 (1H, d), 8.10 (1H, s).

Example 25

Synthesis of 4-[(7-chloro-2,4(1H,3H)-quinazolinedion-3-yl)sulfonyl]-1-hydroxy-naphthalene-2-carboxylic acid (Compound 25)

323 mg (1.00 mmol) of 3-t-butoxycarbonyl-4-hydroxy-1-naphthalenesulfonamide and 381 mg (1.00 mmol) of benzyl 4-chloro-2-N-phenoxycarbonylanthranilate were treated in the same way as in Example 17 to obtain 447 mg (yield 73%) of 4-({[(2-benzyloxycarbonyl-5-chloroanilino) carbonyl]amino}sulfonyl)-1-hydroxy-2-naphthalenecarboxylic acid t-butyl ester. Properties: colorless amorphous, PMR (δ ppm, DMSO-$d_6$): 1.66 (9H, s), 5.34 (3H, s), 6.98 (1H, d), 7.35–7.48 (5H, m), 7.66 (1H, m), 7.81 (1H, m), 7.89 (1H, d), 8.37 (2H, m), 8.44 (1H, s), 8.71 (1H, d), 10.02 (1H, br), 12.52 (1H, br).

Then, from 445 mg (0.72 mmol) of the resultant sulfonylurea product, in the same way, 56 mg (yield 18%: 3 steps) of the above-identified compound was obtained. Properties: colorless crystal, Melting point: >200° C. (decomposition), PMR (δ ppm, DMSO-$d_6$): 7.08 (1H, s), 7.20 (1H, d), 7.63 (1H, t), 7.77 (1H, t), 7.84 (1H, d), 8.42 (1H, d), 8.51 (1H, d), 8.75 (1H, s), 11.57 (1H, s).

Example 26

Synthesis of 5-[(7-chloro-2,4(1H,3H)-quinazolinedion-3-yl sulfonyl]anthranilic acid (Compound 26)

834 mg (2.05 mmol) of 4-benzyloxycarbonylamino-3-t-butoxycarbonylbenzenesulfonamide and 783 mg (2.05 mmol) of benzyl 4-chloro-2-N-phenoxycarbonylanthranilate were treated in the same way as in Example 17 to obtain 1.18 g (yield 83%) of benzyl 2-{[(4-benzyloxycarbonylamino-3-t butoxycarbonylbenzenesulfonylamino)carbonyl]amino}-4-chlorobenzoate. Properties: colorless amorphous, PMR (δ ppm, $CDCl_3$): 1.56 (9H, s), 5.22 (2H, s), 5.37 (2H, s), 7.04 (1H, dd), 7.33–7.42 (10H, m), 7.97 (1H, d), 8.14 (1H, d), 8.45 (1H, d), 8.60 (1H, d), 8.65 (1H, d), 11.01 (1H, s), 11.11 (1H, s).

Then, from 1.17 g (1.69 mmol) of the resultant sulfonylurea product, in the same way, 404 mg (yield 60%: 3 steps) of the above-identified compound was obtained. Properties: colorless crystal, Melting point: >200° C. (decomposition), PMR (δ ppm, DMSO-$d_6$): 6.89 (1H, d), 7.11 (1H, s), 7.23 (1H, d), 7.85 (1H, d), 7.98 (1H, d), 8.51 (1H, s), 11.51 (1H, s).

Example 27

Synthesis of 4-[(7-methoxy-2,4(1H,3H)-quinazolinedion-3-yl)sulfonyl]anthranilic acid (Compound 27)

500 mg (1.23 mmol) of 3-benzyloxycarbonylamino-4-t-butoxycarbonylbenzenesulfonamide and 460 mg (1.22 mmol) of benzyl 4-methoxy-2-N-phenoxycarbonylanthranilate were treated in the same way as in Example 17 to obtain 15 mg (yield 3.1%: 4 steps) of the above-identified compound. Properties: colorless crystal, Melting point: >200° C. (decomposition), PMR (δ ppm, DMSO-$d_6$): 3.82 (3H, s), 6.58 (1H, s), 6.80 (1H, d), 7.16 (1H, d), 7.56 (1H, s), 7.80 (1H, d), 7.90 (1H, d), 11.49 (1H, s).

Example 28

Synthesis of (±)-7-[(7-chloro-2,4(1H,3H)-quinazolinedion-3-yl)sulfonyl]-2-oxo-1H,3H-quinoline-3-carboxylic acid (Compound 28)

400 mg (1.23 mmol) of (±)-3-t-butoxycarbonyl-2-oxo-1H,3H-quinoline-7-sulfonamide and 468 mg (1.23 mmol) of benzyl 4-chloro-2-N-phenoxycarbonylanthranilate were treated in the same way as in Example 17 to obtain 649 mg (yield 86%) of 8-({[(2-benzyloxycarbonyl-5-chloroanilino)carbonyl]amino}sulfonyl)-2-oxo-1,2,3,4-tetrahydro-3-quinoline carboxylic acid t-butyl ester. Properties: colorless amorphous, PMR (δ ppm, $CDCl_3$): 1.32 (9H, s), 3.18–3.30 (2H, m), 3.54 (1H, m), 5.35 (2H, s), 6.85 (1H, m), 7.00 (1H, m), 7.35–7.39 (5H, m), 7.87–7.96 (3H, m), 8.47 (1H, m), 8.78 (1H, br), 10.92 (1H, br).

Then, from 640 mg (1.04 mmol) of the resultant sulfonylurea product, in the same way, 258 mg (yield 55%: 3 steps) of the above-identified compound was obtained. Properties: colorless crystal, Melting point: >200° C. (decomposition), PMR (δ ppm, DMSO-$d_6$): 3.23–3.31 (2H, m), 3.59 (1H, t), 7.07 (1H, d), 7.12 (1H, s), 7.25 (1H, d), 7.86 (1H, d), 7.96 (1H, d), 7.98 (1H, d), 10.84 (1H, s), 11.60 (1H, s).

Example 29

Synthesis of (±)-6-[(7-chloro-2,4(1H,3H)-quinazolinedion-3-yl)sulfonyl]-3-oxo-1,4-benzoxazine-2-carboxylic acid (Compound 29)

300 mg (0.91 mmol) of (±)-2-t-butoxycarbonyl-3-oxo-1,4-benzoxazin-6-sulfonamide and 349 mg (0.91 mmol) of benzyl 4-chloro-2-N-phenoxycarbonylanthranilate were treated in the same way as in Example 17 to obtain 417 mg (yield 74%) of 5-({[(2-benzyloxycarbonyl-5-chloroanilino)carbonyl]amino}sulfonyl)-3-oxo-3,4-dihydro-2H-1,4-benzoxazine-2-carboxylic acid t-butyl ester. Properties: colorless amorphous, PMR (δ ppm, DMSO-$d_6$): 1.29 (9H, s), 5.37 (2H, s), 5.42 (2H, s), 7.19–7.26 (2H, m), 7.37–7.57 (7H, m), 7.97 (1H, d), 8.25 (1H, d), 10.27 (1H, s), 11.25 (1H, s), 12.22 (1H, br).

Then, from 417 mg (0.68 mmol) of the resultant sulfonylurea product, in the same way, 100 mg (yield 32%: 3 steps) of the above-identified compound was obtained. Properties: colorless crystal, Melting point: >200° C. (decomposition), PMR (δ ppm, DMSO-$d_6$): 5.47 (1H, s), 7.11 (1H, s), 7.24 (1H, d), 7.29 (1H, d), 7.76 (1H, s), 7.78 (1H, d), 7.86 (1H, d), 11.25 (1H, s), 11.62 (1H, s).

Example 30

Synthesis of 4-[(7-hydroxy-2,4(1H,3H)-quinazolinedion-3-yl)sulfonyl]anthranilic acid (Compound 30)

620 mg (1.53 mmol) of 3-benzyloxycarbonylamino-4-t-butoxycarbonylbenzenesulfonamide and 550 mg (1.51 mmol) of benzyl 4-hydroxy-2-N-phenoxycarbonylanthranilate were treated in the same way as in Example 17 to obtain 25 mg (yield 4%: 4 steps) of the above-identified compound. Properties: colorless crystal, Melting point: >200° C. (decomposition), PMR (δ ppm, DMSO-$d_6$): 6.48 (1H, s), 6.61 (1H, d), 7.14 (1H, d), 7.51 (1H, s), 7.70 (1H, d), 7.90 (1H, d), 10.80 (1H, s), 11.39 (1H, s).

Example 31

Synthesis of 4-[(7-chloro-2,4(1H,3H)-quinazolinedion-3-yl)sulfonyl]-2-N-propionylanthranilic acid (Compound 31)

840 mg (1.86 mmol) of Compound 17 was dissolved in 8 ml of 1,4-dioxane, 240 μl (2.79 mmol) of propionyl chloride was added dropwise, then the resultant mixture was stirred overnight at 60° C. An excess of water was added to the reaction solution and the mixture was extracted with ethyl acetate. The organic layer thus obtained was washed, dried, and concentrated to obtain a crude product of t-butyl 4-[(7-chloro-2,4(1H,3H)-quinazolinedion-3-yl)sulfonyl]-2-N-propionylanthranilate. The obtained crude product was stirred at room temperature in 3 ml of trifluoroacetic acid for 1 hour, then the reaction solution was concentrated in vacuo to obtain a crude product. This was washed by diethyl ether to obtain 400 mg (yield 48%; 2 steps) of the above-identified compound. Properties: colorless crystal, Melting point:

>200° C. (decomposition), PMR (δ ppm, DMSO-$d_6$): 1.10 (3H, t), 2.45 (2H, dd), 7.11 (1H, s), 7.24 (1H, d), 7.85 (1H, d), 7.88 (1H, d), 8.17 (1H, d), 9.18 (1H, s), 11.07 (1H, s), 11.63 (1H, s).

Example 32

Synthesis of 4-[(6-chloro-2,4(1H,3H)-quinazolinedion-3-yl)sulfonyl]anthranilic acid (Compound 32)

300 mg (0.74 mmol) of 3-benzyloxycarbonylamino-4-t-butoxycarbonylbenzenesulfonamide and 310 mg (0.81 mmol) of benzyl 5-chloro-2-N-phenoxycarbonylanthranilate were treated in the same way as in Example 17 to obtain 75 mg (yield 26%: 4 steps) of the above-identified compound. Properties; colorless crystal, Melting point: >200° C. (decomposition), PMR (δ ppm, DMSO-$d_6$): 7.13–7.20 (2H, m), 7.56 (1H, s), 7.72 (1H, d), 7.82 (1H, s), 7.90 (1H, d), 11.68 (1H, s).

Example 33

Synthesis of 4-[(7-chloro-2,4(1H,3H)-quinazolinedion-3-yl)sulfonyl]-2-N-methanesulfonylanthranilic acid (Compound 33)

200 mg (0.44 mmol) of Compound 17 was treated in the same way as in Example 3 to obtain 81 mg of t-butyl 4-[(7-chloro-2,4(1H,3H)-quinazolinedion-3-yl)sulfonyl]-2-N-methanesulfonylanthranilate. This was used to perform the same debutylation reaction to obtain 53 mg (yield 25%: 2 steps) of the above-identified compound. Properties: colorless crystal, Melting point: >200° C. (decomposition), PMR (δ ppm, DMSO-$d_6$): 3.24 (3H, s), 7.11 (1H, s), 7.25 (1H, d), 7.85–7.91 (2H, m), 8.23 (1H, d), 8.39 (1H, s), 11.05 (1H, br), 11.70 (1H, s).

Example 34

Synthesis of 3-(3-aminobenzenesulfonyl)-7-chloro-2,4-(1H,3H)quinazolinedion methanesulfonic acid salt (Compound 34)

2.15 g (6.10 mmol) of compound 12 was dissolved in 65 ml of THF and 0.4 ml of methanesulfonic acid was added dropwise. To this solution, 200 ml of ether was added and the resultant precipitate was filtered to obtain 2.59 g (yield 95%) of the above-identified compound. Properties: colorless amorphous, PMR (δ ppm, DMSO-$d_6$): 2.35 (3H, s), 6.98 (1H, d), 7.12 (1H, m), 7.25 (1H, m), 7.34 (2H, s), 7.43 (1H, m), 7.86 (1H, s), 11.64 (1H, s).

Evaluation Example 1

Measurement of Chymase Inhibitory Activity

Human heart chymase was purified according to the method of Urata et al. (*J. Biol. Chem.*, 1990, 265, 22348). The inhibitory activity of the quinazoline derivatives of the present invention with respect to chymase was measured in the following manner. That is, the purified enzyme solution was diluted to a suitable concentration with 0.1M tris-hydrochloride buffer (pH=7.5), 1M sodium chloride, and 0.01% TritonX-100 to In obtain an enzyme solution. A 10 mM dimethyl sulfoxide (hereinafter referred to as DMSO) solution of Suc-Ala-Ala-Pro-Phe-MCA (Peptide Institute) was diluted 20-fold at the time of use by 0.1M tris-hydrochlorate, 1M sodium chloride, and 0.01% TritonX-100 to obtain the substrate solution.

75 μl of the enzyme solution warmed to 30° C. was mixed with 5 μl of DMSO solution of the test sample. The mixture was preincubated at 30° C. for 10 minutes. Next, 20 μl of a substrate solution warmed to 30° C. was mixed with the test sample-enzyme mixture and incubated at 30° c. After 10 minutes, 50 μl of 30% acetic acid was added to stop the enzymatic reaction. The amount of the AMC produced was quantified using a fluorescent photometer. At the same time, a blind test was carried out by adding, instead of the test sample solution, 5 μl of DMSO and performing the same reaction. The chymase inhibitory activity was expressed by a rate of inhibition, that is, the 50% inhibition concentration ($IC_{50}$), based on the blind test value.

The quinazoline derivatives of the present invention all strongly inhibited human chymase at concentrations of 100 μm. The $IC_{50}$ values for typical compounds are shown in table 1

TABLE 1

| Example No. | $IC_{50}$ value (μM) | $t_{1/2}$ (min) |
| --- | --- | --- |
| 1 | 0.36 | 78 |
| 2 | 0.14 | 175 |
| 8 | 0.035 | 29 |
| 10 | 0.17 | 167 |
| 12 | 0.44 | 249 |
| 13 | 0.3 | 97 |
| 16 | 0.84 | >240 |
| 17 | 0.14 | 260 |
| 18 | 0.14 | 103 |
| 21 | 0.34 | — |
| 22 | 0.3 | 104 |
| 24 | 0.32 | 79 |
| 27 | 4.0 | 263 |
| 29 | 1.7 | >240 |
| 32 | 1.5 | 74 |
| 34 | 0.36 | 709 |

Evaluation Example 2

Test of Human Chymase Induced Vascular Permeability Exacerbation Reaction

Wister male rats (body weight 200 to 220 g, Charles River Japan) were used. In the backs of the rats from which the hair had been shaved off, 100 μl (20 mU: 1U being amount of enzyme for producing 1 nmol of AMC in 1 minute from Suc-Ala-Ala-Pro-Phe-MCA at pH7.5 and 30° C.) of a solution of the human chymase enzyme solution purified in evaluation Example 1 diluted 100-fold by PBS (phosphate buffered saline) was injected intracutaneously, then immediately thereafter a 0.5% (w/w) Evans Blue solution was administered from the tail artery. After 30 minutes, the rats were sacrificed by draining their blood under anesthesia with ether and the amount of dye leaking out to the back skin was measured. The region of the skin where the dye leaked out was cut off and 1.0 ml of 1N KOH solution was added and the resultant mixture was allowed to stand at 37° C. overnight. Next, 4 ml of an acetone-0.6N phosphoric acid (13:5) mixture was added to extract the dye. The absorbance at 650 nm of the supernatant was measured. The calibration curve for measurement of the amount of the dye leaked out was prepared by injecting Evans Blue solution so as to give 10, 20, 30, 40, and 50 μg in the rat back skin and extracting the dye by the above method. Similarly, the amount of dye when administering intracutaneously 100 μl of the solution of the same composition but not containing human chymase was used as the control.

Next, 10 mg/kg of the compound of Example 18 was orally administered. 30 minutes later, 100 μl (20 mU) of human chymase the same as the non-drug administered group was injected intracutaneously and the amount of dye leaked out similarly measured. The rate of suppression of the amount of dye leakage due to the compound was calculated according to the following calculation formula. The rate of suppression for the compound of Example 18 was 64%.

Rate of suppression of amount of leakage of dye (%)=[(amount of leakage of dye of compound administered group−amount of leakage of dye of control group)÷(amount of leakage of dye of non-compound administered group−amount of leakage of dye of control group)]×100.

It is known that vascular permeability is exacerbated when inflammation is caused by an inflammation causing substance. Further, suppression of the exacerbation of vascular permeability has become one of the indicators for evaluation of anti-inflammation agents. In general, it is known that the histamine released by the degranulation of mast cells exacerbate the vascular permeability. The fact that a quinazoline derivative suppresses the exacerbation of vascular permeability due to the intracutaneous administration of chymase shows that the quinazoline derivative suppresses inflammation involving mast cells caused by the chymase.

Evaluation Example 3

Test of Stability in Human Plasma

Human plasma was diluted two-fold with 50 mM sodium phosphate buffer (pH=7.2) for use as the test plasma solution. The test sample was made a DMSO solution of 1 mM concentration.

198 μl of the above two-fold diluted plasma solution warmed to 37° C. was added to 2 μl of the test sample DMSO solution and the resultant mixture was stirred and incubated at 37° C. After 0, 5, and 15 minutes, 800 μl of acetonitrile was mixed with the test sample-plasma mixture to remove the protein, then a centrifugation operation (12,000 rpm, 1 minute) was carried out and the supernatant obtained. This was diluted two-fold with distilled water and measured for of the test sample by HPLC analysis.

For the rate of recovery from the plasma, the rates of recovery at different times were calculated based on a calibration line of the test sample in a DMSO standard solution. The half-life ($t_{1/2}$) in plasma was calculated by exponential recurrence analysis from the rates of recovery of these different times. The half-lives ($t_{1/2}$) in plasma of representative compounds are shown in Table 1.

Preparation Example 1

Production of Tablets 100.0 g of Compound 1 was mixed with microcrystalline cellulose in an amount of 22.5 g and magnesium stearate in an amount of 2.5 g and then tabletized by a single-action type tabletizing machine to produce tablets each containing 200 mg of Compound 1 and having a diameter of 9 mm and a weight of 250 mg.

Preparation Example 2

Production of Granules 30 g of Compound 1 was mixed well with lactose in an amount of 265 g and magnesium stearate in an amount of 5 g. The mixture was pressed molded, then pulverized and the granules sieved to obtain excellent 10% granules of 20 to 50 mesh.

Preparation Example 3

Production of Suppository

Vitepsol H-15 (made by Dynamite Nobel Co.) was warmed to melt. To this was added Compound 1 to a concentration of 12.5 mg/ml. This was homogeneously mixed, then was added in 2 ml amounts to a rectal suppository mold and cooled to obtain rectal suppositories each containing 25 mg of the Compound 1.

INDUSTRIAL APPLICABILITY

The quinazoline derivative of the present invention inhibits chymase and further suppresses the exacerbation of vascular permeability induced by chymase, and therefore, is useful as a medicament for the prevention or treatment of allergic diseases or rheumatic diseases or cardiac and circulatory system diseases arising due to the abnormal exacerbation of angiotensin II production. Examples of such diseases are inflammatory diseases for which mast cells are predicted as being closely related, for example, bronchial asthma, eczema, atopic dermatitis, mastocytosis, scleriasis, rheumatoid arthritis, cardiac and circulatory system diseases due to the abnormal exacerbation of Ang ii production, for example, cardiac insufficiency, hypercardia, stasis cardiac diseases, hypertension, arteriosclerosis, peripheral circulatory disorders, revasoconstriction after PTCA, diabetic renal disorders or non-diabetic renal disorders, coronary diseases including myocardial infarction, angioendothelia, or vascular disorders accompanying arterialization or atheroma.

What is claimed is:
1. A quinazoline derivative having the following formula (1) or a pharmaceutically acceptable salt thereof:

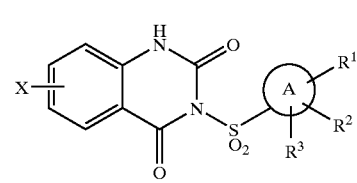

wherein the ring A represents an aryl group:
$R^1$ represents (a) hydroxyl group, (b) an amino group, (c) a $C_1$ to $C_4$ lower alkylamino group which may be substituted with a COOH group, (d) a $C_7$ and $C_{10}$ lower aralkylamino group which may be substituted with a COOH group, (e) an amino group acylated with a $C_1$ to $C_4$ lower aliphatic acid which may be substituted with a COOH group, (f) an amino group acylated with an aromatic ring carboxylic acid which may be substituted with a COOH group, (g) an amino group acylated with a heteroaromatic ring carboxylic acid which may be substituted with a COOH group, (h) an amino group sulfonylated with a $C_1$ to $C_4$ lower alkanesulfonic acid which may be substituted with a COOH group, (i) an amino group sulfonylated with an aromatic ring sulfonic acid which may be substituted with a COOH group, (j) an amino group sulfonylated with a heteroaromatic ring sulfonic acid which may be substituted with a COOH group, (k) a $C_1$ to $C_4$ lower alkyl group substituted with a COOH group, or (l) a $C_2$ to $C_4$ lower alkenyl group which may be substituted with a COOH group;
$R^2$ represents (a) a $C_1$ to $C_4$ lower alkyl group substituted with a COOH group, a halogen atom, a $C_1$ to $C_4$ lower alkoxy group, an amino group, a methylamino group, a dimethylamino group, a carboxymethylamino group or a carboxyethylamino group, (b) a halogen atom, (c) a hydroxyl group, (d) a $C_1$ to $C_4$ lower alkoxyl group, (e) an amino group, (f) a $C_1$ to $C_4$ lower alkylamino group which may be substituted with a COOH group, a halogen atom or a $C_1$ to $C_4$ lower alkoxy group, (g) a $C_7$ to $C_{12}$ aralkylamino group which may be substituted with a COOH group, a halogen atom or a $C_1$ to $C_4$ lower alkoxy group, (h) an amino group acylated with a $C_1$ to $C_4$ lower aliphatic acid which may be substituted with a COOH group, (i) an amino group acylated with an aromatic ring carboxylic acid which may be substituted with a COOH group, (j) an amino group acylated with a heteroaromatic ring carboxylic acid which may be substituted with a COOH group, (k) an amino group sulfonylated with a $C_1$ to $C_4$ lower alkanesulfonic acid which may be substituted with a COOH group, (l) an amino group sulfonylated with an aromatic ring sulfonic acid which may be substituted with a COOH group, (m) an amino group sulfonylated with a heteroaromatic ring sulfonic acid which may be substituted with a COOH group, or (n) a COOH group or $R^3$ represents (a) a hydrogen atom, (b) a $C_1$ to $C_4$ lower alkyl group which may be substituted with a COOH group, a halogen atom, a $C_1$ to $C_4$ lower alkoxy group, an amino group, a methylamino group, a dimethylamino group, a carboxymethylamino group or a carboxyethylamino group, (c) a halogen atom, (d) a hydroxyl group, (e) a $C_1$ to $C_4$ lower alkoxyl group, (f) an amino group, (g) a $C_1$ to $C_4$ lower alkylamino group which may be substituted with a COOH group, a halogen atom or a $C_1$ to $C_4$ lower alkoxy group, (h) a $C_7$ to $C_{12}$ aralkylamino group which may be substituted with a COOH group, a halogen atom or a $C_1$ to $C_4$ lower alkoxy group, (i) an amino group acylated with a $C_1$ to $C_4$ lower aliphatic acid which may be substituted with a COOH group, (j) an amino group acylated with an aromatic ring carboxylic acid which may be substituted with a COOH group, (k) an amino group acylated with a heteroaromatic ring carboxylic acid which may be substituted with a COOH group, (l) an amino group sulfonylated with a $C_1$ to $C_4$ lower alkanesulfonic acid which may be substituted with a COOH group, (m) an amino group sulfonylated with an aromatic ring sulfonic acid which may be substituted with a COOH group, (n) an amino group sulfonylated with a heteroaromatic ring sulfonic acid which may be substituted with a COOH group, or (o) a COOH group or when the ring A is benzene ring, $R^1$ and $R^2$ may form, together with the substituting benzene ring, (a) a tetrahydroquinoline ring or (b) a benzoxazine ring which may be substituted with a COOH group and in which the carbon atom in the ring may form a carbonyl group and $R^3$ is the same as defined above; and X represents (a) a hydrogen atom, (b) a $C_1$ to $C_4$ lower alkyl group, (c) a $C_1$ to $C_4$ lower alkoxy group, (d) a halogen atom, (e) a hydroxyl group, (f) an amino group, or (g) a nitro group.

2. A quinazoline derivative or a pharmaceutically acceptable salt thereof as claimed in claim 1, wherein, in the formula (1), $R^1$ is a hydroxyl group, an amino group, a $C_1$ to $C_4$ lower alkylamino group substituted with a COOH group, or an amino group acylated with a $C_1$ to $C_4$ lower aliphatic acid substituted with a COOH group.

3. A quinazoline derivative or a pharmaceutically acceptable salt thereof as claimed in claim 1, wherein, in the formula (1), $R^2$ is a COOH group.

4. A quinazoline derivative or a pharmaceutically acceptable salt thereof as claimed in claim 1, wherein $R^3$ in the formula (1) is a hydrogen atom.

5. A pharmaceutical composition comprising as an effective ingredient a pharmaceutically effective amount of a quinazoline derivative or the pharmaceutically acceptable salt thereof according to claim 1 and a pharmaceutically acceptable carrier therefor.

6. A chymase composition inhibitor having as an effective ingredient a quinazoline derivative or its pharmaceutically acceptable salt according to claim 1, and a pharmaceutically acceptable carrier therefor.

7. A method for treatment of allergic diseases or rheumatic diseases comprising administering to a patient in need of such treatment an effective amount of a quinazoline derivative or salt thereof according to claim 1.

8. A method for treatment of bronchial asthma, eczema, atopic dermatitis, mastocytosis, scleriasis or rheumatoid arthritis comprising administering to a patient in need of such treatment an effective amount of a quinazoline derivative or salt thereof according to claim 1.

9. A method for treatment of cardiac and circulatory system diseases due to the abnormal exacerbation of Angiotensin II production comprising administering to a patient in need of such treatment an effective amount of a quinazoline derivative or salt thereof according to claim 1.

10. A method for treatment of cardiac insufficiency, hypercardia, stasis cardiac diseases, hypertension, arteriosclerosis, peripheral circulatory diseases, revasoconstriction after PTCA, diabetic renal disorders or non-diabetic renal disorders, cardiac infarction, angioendothelia or vascular disorders accompanying arterialization and atheroma comprising administering to a patient in need of such treatment an effective amount of a quinazoline derivative or salt thereof according to claim 1.

11. A pharmaceutical composition comprising as an effective ingredient a pharmaceutically effective amount of a quinazoline derivative or a pharmaceutically acceptable salt thereof as claimed in claim 2, and a pharmaceutically acceptable carrier therefor.

12. A pharmaceutical composition comprising as an effective ingredient a pharmaceutically effective amount of a quinazoline derivative or a pharmaceutically acceptable salt thereof as claimed in claim 3, and a pharmaceutically acceptable carrier therefor.

13. A pharmaceutical composition comprising as an effective ingredient a pharmaceutically effective amount of a quinazoline derivative or a pharmaceutically acceptable salt thereof as claimed in claim 4, and a pharmaceutically acceptable carrier therefor.

14. A quinazoline derivative having the following formula (1) and a pharmaceutically acceptable salt thereof:

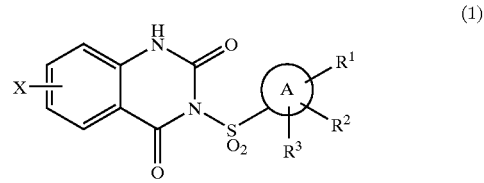

(1)

wherein the ring A represents an aryl group:

$R^1$ represents (a) hydroxyl group, (b) a $C_1$ to $C_4$ lower alkylamino group which may be substituted with a COOH group, (c) a $C_7$ and $C_{10}$ lower aralkylamino group which may be substituted with a COOH group, (d) an amino group acylated with a $C_1$ to $C_4$ lower aliphatic acid which may be substituted with a COOH group, (e) an amino group acylated with an aromatic ring carboxylic acid which may be substituted with a COOH group, (f) an amino group acylated with a heteroaromatic ring carboxylic acid which may be substituted with a COOH group, (g) an amino group sulfonylated with a $C_1$ to $C_4$ lower alkanesulfonic acid which may be substituted with a COOH group, (h) an amino group sulfonylated with an aromatic ring sulfonic acid which may be substituted with a COOH group, (i) an amino group sulfonylated with a heteroaromatic ring sulfonic acid which may be substituted with a COOH group, (j) a $C_1$ to $C_4$ lower alkyl group substituted with a COOH group, or (k) a $C_2$ to $C_4$ lower alkenyl group which may be substituted with a COOH group;

$R^2$ and $R^3$ may be the same or different and represent (a) a hydrogen atom, (b) a $C_1$ to $C_4$ lower alkyl group which may be substituted with a COOH group, a halogen atom, a $C_1$ to $C_4$ lower alkoxy group, an amino group, a methylamino group, a dimethylamino group, a carboxymethylamino group or a carboxyethylamino group, (c) a halogen atom, (d) a hydroxyl group, (e) a $C_1$ to $C_4$ lower alkoxyl group, (f) an amino group, (g) a $C_1$ to $C_4$ lower alkylamino group which may be substituted with a COOH group, a halogen atom or a $C_1$ to $C_4$ lower alkoxy group, (h) a $C_7$ to $C_{12}$ aralkylamino group which may be substituted with a COOH group, a halogen atom or a $C_1$ to $C_4$ lower alkoxy group, (i) an amino group acylated with a $C_1$ to $C_4$ lower aliphatic acid which may be substituted with a COOH group, (j) an amino group acylated with an aromatic ring carboxylic acid which may be substituted with a COOH group, (k) an amino group acylated with a heteroaromatic ring carboxylic acid which may be substituted with a COOH group, (l) an amino group sulfonylated with a $C_1$ to $C_4$ lower alkanesulfonic acid which may be substituted with a COOH group, (m) an amino group sulfonylated with an aromatic ring sulfonic acid which may be substituted with a COOH group, (n) an amino group sulfonylated with a heteroaromatic ring sulfonic acid which may be substituted with a COOH group, or (o) a COOH group or when the ring A is benzene ring, $R^1$ and $R^2$ may form, together with the substituting benzene ring, (a) a tetrahydroquinoline ring or (b) a benzoxazine ring which may be substituted with a COOH group and in which the carbon atom in the ring may form a carbonyl group and $R^3$ is the same as defined above; and X represents (a) a hydrogen atom, (b) a $C_1$ to $C_4$ lower alkyl group, (c) a $C_1$ to $C_4$ lower alkoxy group, (d) a halogen atom, (e) a hydroxyl group, (f) an amino group, or (g) a nitro group.

15. A quinazoline derivative or a pharmaceutically acceptable salt thereof as claimed in claim 1, wherein said compound is selected from the group consisting of
3-(3-amino-4-chlorobenzenesulfonyl)-7-chloro-2,4(1H,3H)-quinazolinedione,
3-(4-amino-3,5-dichlorobenzenesulfonyl)-7-chloro-2,4(1H,3H)-quinazolinedione,
4-[(7-chloro-2,4(1H,3H)quinazolinedion-3-yl)sulfonyl] anthranilic acid,
4-[(7-chloro-2,4(1H,3H)-quinazolinedion-3-yl)sulfonyl] anthranilic acid monosodium salt,
3-(3-amino-4-methoxybenzenesulfonyl)-7-chloro-2,4(1H,3H)-quinazolinedione,
5-[(7-chloro-2,4(1H,3H)-quinazolinedion-3-yl)sulfonyl] anthranilic acid,
4-[(7-methoxy-2,4(1H,3H)-quinazolinedion-3-yl)sulfonyl] anthranilic acid,
4-[(7-hydroxy-2,4(1H,3H)-quinazolinedion-3-yl)sulfonyl] anthranilic acid and
4-[(6-chloro-2,4(1H,3H)-quinazolinedion-3-yl)sulfonyl] anthranilic acid.

16. A pharmaceutical composition comprising as an effective ingredient a pharmaceutically effective amount of a quinazoline derivative or a pharmaceutically acceptable salt thereof according to claim 14 and a pharmaceutically acceptable carrier therefore.

17. A chymase composition inhibitor having as an effective ingredient a quinazoline derivative or a pharmaceutically acceptable salt thereof according to claim 14 and a pharmaceutically acceptable carrier therefore.

* * * * *

UNITED STATES PATENT AND TRADEMARK OFFICE
CERTIFICATE OF CORRECTION

PATENT NO. : 6,867,214 B1
APPLICATION NO. : 09/763213
DATED : March 15, 2005
INVENTOR(S) : Harukazu Fukami et al.

It is certified that error appears in the above-identified patent and that said Letters Patent is hereby corrected as shown below:

Column 2,
Line 55, "with a carboxylic acid group, a $C_7$ and $C_{10}$ lower" should be -- "with a carboxylic acid group, a $C_7$ to $C_{10}$ lower --.

Column 24,
Line 46, "substituted with a COOH group, (d) a $C_7$ and $C_{10}$ lower" should be -- substituted with a COOH group, (d) a $C_7$ to $C_{10}$ lower --.

Column 26,
Line 65, "COOH group, (c) $C_7$ and $C_{10}$ lower aralkylamino" should be -- COOH group, (c) $C_7$ to $C_{10}$ lower aralkylamino --.

Signed and Sealed this

Twenty-seventh Day of June, 2006

JON W. DUDAS
*Director of the United States Patent and Trademark Office*